United States Patent [19]

Diel

[11] 4,160,833
[45] Jul. 10, 1979

[54] 1,2,4-BENZOTRIAZINE-1,4-DI-N-OXIDE DERIVATIVES

[75] Inventor: Peter J. Diel, Muttenz, Switzerland

[73] Assignee: Ciba-Geigy Corporation, Ardsley, N.Y.

[21] Appl. No.: 843,473

[22] Filed: Oct. 19, 1977

Related U.S. Application Data

[63] Continuation-in-part of Ser. No. 437,415, Jan. 28, 1974, abandoned.

[30] Foreign Application Priority Data

Feb. 2, 1973 [CH] Switzerland .................. 1555/73
Sep. 5, 1973 [CH] Switzerland .................. 12733/73

[51] Int. Cl.² ............... C07D 253/08; A61K 31/53
[52] U.S. Cl. ................................. 424/249; 544/183
[58] Field of Search ...................... 544/183; 424/249

[56] References Cited

U.S. PATENT DOCUMENTS

| 3,957,779 | 5/1976 | Seng et al. ............ 544/183 |
| 3,985,745 | 10/1976 | Diel ...................... 544/183 |
| 3,991,189 | 11/1976 | Seng et al. ............ 544/183 |

OTHER PUBLICATIONS

Mason et al., *J. Chem. Soc.*, Part B, pp. 911–916 (1970).

*Primary Examiner*—John M. Ford
*Attorney, Agent, or Firm*—Harry Falber

[57] ABSTRACT

This invention concerns new 1,2,4-benzotriazine-1,4-di-N-oxide derivatives corresponding to the formula

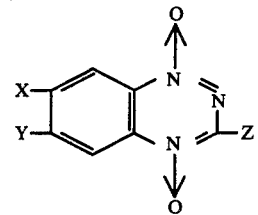

wherein
X and Y each independently represent hydrogen, alkyl or alkoxy having 1 to 4 carbon atoms, phenoxy, or halogen, and
Z stands for a group of the formula

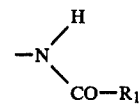

wherein $R_1$ represents alkoxy having 1 to 6 carbon atoms, aralkoxy having 1 to 4 carbon atoms within the alkoxy portion, or a heterocyclic radical having 5 to 6 ring members, with the proviso that if the heterocyclic radical contains an N-atom as ring member, this N-atom is not attached to the carbonyl group, or for a group of the formula

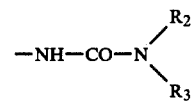

wherein $R_2$ and $R_3$ each independently represents aralkyl containing 1 to 4 carbon atoms in the alkyl portion, or a heterocyclic radical having 5 to 6 ring members, 1 or 2 of which are hetero atoms, or a group of the formula

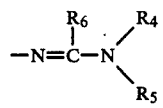

wherein $R_4$ and $R_5$ each independently represents hydrogen or alkyl having 1 to 4 carbon atoms, and $R_6$ represents hydrogen or methyl,
agents containing the new compounds and the use of the new compounds for the control of microorganisms, as feed additives for animals of commercial value, and for the protection of materials.

8 Claims, No Drawings

1,2,4-BENZOTRIAZINE-1,4-DI-N-OXIDE DERIVATIVES

RELATED APPLICATION

This application is a continuation-in-part of application Ser. No. 437,415, filed Jan. 28, 1974, now abandoned.

The present invention relates to new 1,2,4-benzotriazine-1,4-di-N-oxide derivatives, to agents containing the new compounds, and to the use of the new compounds for the control of microorganisms, as feed additives for animals for commercial value, and for the protection of materials.

The new 1,2,4-benzotriazine-1,4-di-N-oxide derivatives correspond to the general formula I

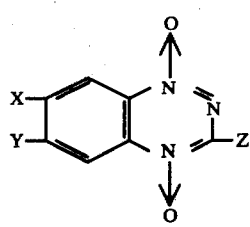

wherein
X and Y each independently represent hydrogen, alkyl, or alkoxy having 1 to 4 carbon atoms, phenoxy or halogen, and
Z stands for a group of the formula

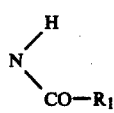

$R_1$ represents alkoxy, having 1 to 6 carbon atoms, aralkoxy having 1 to 4 carbon atoms within the alkoxy portion, or a heterocyclic radical having 5 to 6 ring members with the proviso that if the heterocyclic radical contains an N-atom as ring member, this N-atom is not attached to the carbonyl group, or for a group of the formula

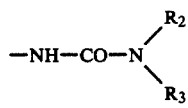

wherein $R_2$ and $R_3$ each independently represent aralkyl containing 1 to 4 carbon atoms within the alkyl portion or a heterocyclic radical having 5 to 6 ring-members, 1 or 2 of which are hetero atoms, or for a group of the formula

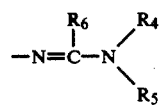

wherein $R_4$ and $R_5$ each independently represents hydrogen or alkyl having 1 to 4 carbon atoms, and $R_6$ represents hydrogen or methyl, preferably hydrogen.

As aralkyl groups, $R_2$ and $R_3$ represent, in particular, the benzyl or phenethyl group, which can be substituted in the phenyl radical by lower alkyl, lower alkoxy, halogen, nitro, lower haloalkyl, with suitable lower alkyl or lower alkoxy groups being those having 1 to 4 carbon atoms, halogen being fluorine, chlorine, bromine or iodine, and lower haloakyl being, in particular, the trifluoromethyl group.

Aralkoxy groups denoted by $R_1$ are, in particular, the benzyloxy or phenethoxy group, whereby the phenyl radicals present in these groups can be substituted in the manner described above in the case of the definition of the meaning of aralkyl.

Heterocyclic radicals denoted by $R_1$, $R_2$ and $R_3$ are, in particular, radicals derived from pyridine, furan, thiophene, pyrrole or pyrimidine.

Compounds of formula I in which Z represents —NH—CO—$R_1$, are prepared by the reaction of compounds of the formula II

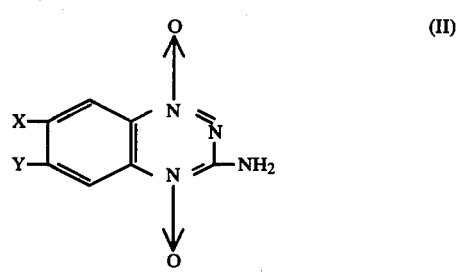

with acid halides of formula III

wherein Hal denotes a halogen atom, and radicals X, Y and $R_1$ have the meanings given under formula I. This reaction can be performed in an advantageous manner in solvents such as, e.g. dioxane, tetrahydrofuran, benzene, toluene or an aqueous-organic two-phase system in the presence of alkali hydroxide or of a tertiary base (e.g. pyridine), at a temperature of 30°–70° C., with acid chlorides or chlorocarbonic acid esters (for synthesis of compounds of formula II see J. Chem. Soc. 1957, pp. 3182–94 and 'Angew. Chemie' 84, 21 (1972) p. 1061).

Compounds of formula I in which Z represents

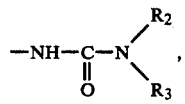

are prepared
(a) by reaction of a compound of formula IV

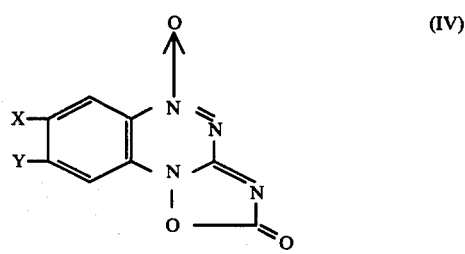

with amines of formula V

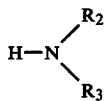

wherein X and Y, R₂ and R₃ have the meanings given under formula I, in an inert solvent, or without solvent as described by Ley and Seng ('Angew. Chemie' 84, 21 (1972) p. 1061);

(b) by reaction of a compound of formula II with carbamic acid halides of formula VI

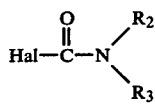

wherein Hal represents a halogen atom, and R₂ and R₃ have the meanings given under formula I.

Compounds of formula I in which Z represents

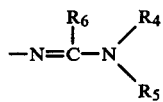

are prepared by the reaction of compounds of formula II with compounds of formula VIII

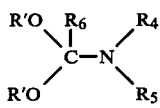

wherein R₄, R₅ and R₆ have the meanings given under formula I and R' represents methyl or ethyl, in an inert solvent such as, e.g. alochol, preferably methylcellosolve.

The new 1,2,4-benzotriazine-1,4-di-N-oxide derivatives of formula I are characterised by a good microbicidal action, and accordingly have a general and extensive field of application for the control of pathogenic microorganisms. They exhibit in particular an excellent action in the case of respiratory diseases (CRD) caused by E. coli airsacculitis in poultry. They movoever have a good inhibiting and destroying action against gram-positive and gram-negative bacteria, as well as against fungi. Furthermore, they are very effective against virulent germs in animals.

The compounds of formula I and the agents containing them can be employed, by virtue of their action, for the control of harmful microorganisms. For this purpose they can be in the form of solutions, emulsions, suspensions, scattering powders, ointments and creams for the preservation of organic materials, such as wood, paper, plastics, coating agents, etc., and also as disinfectants, e.g. in soaps, cosmetic articles, detergents and rinsing baths.

The application of the antimicrobial compounds of the present invention is possible on a very wide basis, particularly for the protection of organic substrates against infestation by harmful and pathogenic microorganisms. The mentioned antimicrobic agents are thus suitable as preservatives and disinfectants for commercial products of all kinds.

The following may be mentioned as examples of commercial products which can be preserved by means of compounds of formula I according to the invention; glues, bonding agents, coating agents, textile auxiliaries or finishing agents, dyeing and printing pastes and similar preparations based on organic and inorganic dye-stuffs and pigments, also products containing as ingredients casein or other organic compounds. In addition, wall and ceiling paints, e.g. those containing albuminous dye bonding agent, are protected against infestation by pests by an addition of the compounds according to the invention.

The action of the compounds according to the invention can also be utilised in the preserving and disinfecting finishing of plastics. It is advantageous where plasticizers are used for the antimicrobial additive to be dissolved or dispersed in the plasticizer when being added to the plastics.

The compounds according to the invention are used with advantage for imparting to fibres and textiles a preserving and disinfecting finish, whereby the said compounds can be applied to natural and synthetic fibres on which they then exhibit a permanent action against harmful (also pathogenic) microorganisms, e.g. fungi and bacteria. The addition of the compounds can be made before, simultaneously with or after a treatment of these textiles with other substances, e.g. dyeing or printing pastes, fireproofing agents, soft-handle agents and other finishing agents, etc.

The content of active substances according to the present invention can be, depending on the purpose of application, between 0.1 and 50 g, preferably between 1 and 30 g, of active substance per liter of treatment liquid.

The active substances according to the present invention can be used on their own or together with other known antimicrobial textile-protective agents.

Textiles which can be finished or preserved are both fibres of natural origin, such as cellulose-containing fibres, e.g. cotton, or polypeptide-containing fibres, e.g. wool or silk; or fibre materials of synthetic origin, such as those based on polyamide, polyacrylonitrile or polyester; or mixtures of these fibres.

The textile materials are usually adequately protected by a content of 0.01 to 5%, preferably 0.1 to 3%, of active substance, relative to the weight of the textile materials, against fungus and bacteria infestation.

By a combination of the compounds according to the invention with interface-active, especially wash-active, substances, detergents and cleaning agents are obtained which have an excellent antibacterial action.

The detergents and cleansing agents can be in any desired form, e.g. in a liquid, pasty, solid, flaky or granular form. The compounds according to the invention can be incorporated into anion-active compounds, such as soaps and other carboxylates (e.g. alkali salts of higher fatty acids), derivatives of sulphur-oxygen acids (e.g. sodium salt of dodecylbenzenesulphonic acid, water-soluble salts of sulphuric acid monoesters of higher-molecular alcohols or their polyglycol ethers, such as, for instance, soluble salts of dodecyl alcohol-sulphate or of dodecyl alcohol polyglycol ether sulphate), derivatives of phoshorus-oxygen acids (e.g. phosphates), derivatives with acid (electrophilic) nitrogen in the hydrophilic group (e.g. disulphine salts); also into cation-active surface-active agents, such as amines and their salts (e.g. lauryldiethylenetriamine), onium compounds, amine oxides or nonionic surface-active agents such as polyhydroxy compounds, surface-active agents based on mono- or polysaccharide, higher-molecular acetylene glycols, polyglycol ethers (e.g. polyglycol ethers of higher fatty alcohols, polyglycol ethers of higher-molecular akylated phenols), or mixtures of various surface-active agents. The antimicrobial effectiveness of the said compounds is retained to its full extent. The active-substance content in the detergents and cleansing agents, relative to the weight of these agents, is generally 0.01 to 5%, in most cases 0.1 to 3%. Aqueous preparations of such detergents and cleansing agents, which contain compounds according to the invention, can be used, e.g. for the antimicrobial finishing of textile materials. They are likewise suitable as antimicrobial cleansing agents in the food and drink industry, e.g. in breweries, dairies, cheese factories and slaughter houses.

Furthermore, the compounds according to the invention can also be incorporated into cosmetic preparations, in consequence of which there is additionally imparted to these products an antimicrobial action. In general, an active-substance content of 0.01 to 5%, preferably of 0.1 to 3%, relative to the total weight of the product, suffices.

For the purpose of disinfection and preservation, the compounds of formula I may also be used in combination with known antimicrobial agents. These include, e.g.:

Halogens and halogen compounds with active halogen e.g. sodium hypochlorite, calcium hypochlorite, chloride of lime, sodium-p-toluenesulphochloramide, p-toluenesulphodichloramide, N-chlorosuccinimide, 1,3-dichloro-5,5-dimethylhydantoin, trichloroisocyanuric acid, potassium dichloroisocyanurate, iodine, iodine trichloride, complex compounds of iodine and iodine trichloride with surfactants such as polyvinylpyrrolidone, alkylphenoxypolyglycols, polyoxypropylene glycols, alkylaminoethanesulphonic acids and -sulphonates, alkylarylsulphonates, and quaternary ammonium compounds.

Boron compounds e.g. boric acid, borax.

Organometallic compounds e.g. bis-tributyltin oxide, triphenyltin hydroxide, tributyltin salicylate, tributyltin chloride, phenylmercury borate, phenylmercury acetate.

Alcohols e.g. hexyl alcohol, trichloroisobutyl alcohol, 1,2-propylene glycol, triethylene glycol, benzyl alcohol, 4-chlorobenzyl alcohol, 2,4- and 3,4-dichlorobenzyl alcohol, 2-phenylethyl alcohol, 2-(4-chlorophenyl)-ethyl alcohol, ethylene glycol monophenyl ether, menthol, linalool and 2-bromo-2-nitro-propanediol-1,3.

Aldehydes e.g. formaldehyde, paraformaldehyde, glutaraldehyde, benzaldehyde, 4-chlorobenzaldehyde, 2,4- and 3,4-dichlorobenzaldehyde, cinnamaldehyde, salicylic aldehyde, 3,5-dibromosalicylic aldehyde, 4-hydroxybenzaldehyde, anisaldehyde and vanillin.

Carboxylic acids and derivatives e.g. trichloroacetic acid, monobromoacetic acid glycol ester, Na- and Ca-propionate, caprylic acid, undecylenic acid, Zn-undecylenate, sorbic acid, K- and Ca-sorbate, lactic acid, malonic acid, aconitic acid, citric acid, benzoic acid, 4-chlorobenzoic acid, benzoic acid benzyl ester, salicylic acid, 4-chlorosalicylic acid-n-butylamide, salicylanilide, 3,4',5-tribromosalicylanilide, 3,3',4',5-tetrachlorosalicylanilide, 4-hydroxybenzoic acid, 4-hydroxybenzoic acid ethyl ether, gallic acid, mandelic acid, phenylpropiolic acid, phenoxyacetic acid, dehydracetic acid.

Phenols e.g. phenol, mono- and polychlorophenols, cresols, 4-chloro-3-methylphenol, 4-chloro-3,5-dimethylphenol, thymol, 4-chlorothymol, 4-t-amylphenol, saligenin, 4-n-hexylresorcin, carvacrol, 2-phenylphenol, 2-benzyl-4-chlorophenol, 2,2'-dihydroxy-5,5'-dichlorodiphenylmethane, 2,2'-dihydroxy-3,3',5,5',6,6'-hexachloro-diphenylmethane, 2,2'-dihydroxy-5,5'-dichloro-diphenylsulphide, 2,2'-dihydroxy-3,3',5,5'-tetrachlorodiphenylsulphide, 2-hydroxy-2',4,4'-trichlorodiphenyl ether and dibromosalicyl.

Quinones e.g. 2,5-dimethylquinone, 2,3,5,6-tetrachloro-benzoquinone, 1,4-2,3-dichloro-1,4-naphthoquinone.

Carbonic acid derivatives e.g. pyrocarbonic acid diethyl ester, tetramethylthiuram disulphide, 3,4,4'-trichloro-N,N'-diphenylurea, 3-trifluoromethyl-4,4'-dichloro-N,N'-diphenylurea, N-3-trifluoromethylphenyl-N'-2-ethylhexyl-urea, 1,6-bis-(4'-chlorophenyl-diguanidino)-hexane, dodecylmethyl-quanidine 1 acetate, ammonium rhodanide, 4,4'-diamidino-α, ω-di-phenoxyhexane.

Amines e.g. dodecylpropylenediamine, dodecyldiethylenetriamine and diaminobenzene-dihydroiodide.

Quaternary ammonium compounds e.g. alkyl-dimethyl-benzyl-ammonium chloride, alkyl-dimethyl-ethyl-benzyl-ammonium chloride, dodecyl-dimethyl-3,4-dichlorobenzyl-ammonium chloride, dodecyl-di-(2-hydroxyethyl)-benzyl-ammonium chloride, dodecyl-di-(2-hydroxyethyl)-benzyl-ammonium-pentachlorophenolate, dodecyl-di-(2-hydroxyethyl)-benzyl-ammonium-4-methyl benzoate, dodecyl-dimethyl-phenoxyethyl-ammonium bromide, 4-diisobutyl-phenoxyethoxyethyl chloride, 4-diisobutyl-cresoxyethoxyethyl-dimethyl-benzyl-ammonium chloride, dimethyl-didecyl-ammonium chloride, cetyltrimethylammonium bromide, dodecyl-pyridinium chloride, cetylpyridinium chloride, dodecyl-isoquinolinium chloride, decamethylene-bis-4-aminoquinaldinium dichloride, α-(p-tolyl)-dodecyl-trimethyl-ammonium methosulphate, (dodecanoyl-N-methyl-aminoethyl)-(phenylcarbamoyl-methyl)-dimethylammonium chloride.

Quaternary phosphonium compounds e.g. dodecyltriphenyl-phosphonium bromide.

Ampheteric compounds e.g. dodecyl-di-(aminoethyl)-glycine.

Heterocyclic compounds e.g. 2-mercaptopyridine-N-oxide, Na- and Zn-salt of 2-mercaptopyridine-N-oxide, 2,2'-dithiopyridine-1,1'-di-N-oxide, 8-hydroxyquinoline, 5-chloro-8-hydroxyquinoline, 5-chloro-7-iodine-8-hydroxyquinoline, 5,7-dichloro-8-hydroxyquinoline, 5,7-dichloro-8-hydroxyquinaldine, bis-2-methyl-4-amino-quinolyl-carbamide-hydrochloride, 2-mercaptobenzthiazole, 2-(2'-hydroxy-3',5'-dichlorophenyl)-5-chlorobenzimidazole, 2-aminoacridine-hydrochloride, 5,6-dichlorobenzoxazolone, 1-dodecyl-2-iminoimidazoline-hydrochloride and 6-chloro-benzisothiazolone.

The compounds of the present invention also have an excellent growth-promoting action in the case of animals of commercial value, e.g. pigs and poultry, as well as ruminants, such as cattle or sheep.

The active substances can be administered to the animals perorally or via the abomasum, or by means of injection, in the form of solutions, emulsions, suspensions, powders, tablets, boluses and capsules, either as a single dose or as repeated doses. The active substances or mixtures containing them may also be added to the feed or to the drinking trough, or can be contained in so-called feed pre-mixings.

By virtue of their wide microbicidal range of action, the compounds of the present invention can also be used in veterinary medicine for the control of pathogenic microorganisms on and in the animal, particularly on the skin and in the intestinal tract and urogenital system. For the control of pathogenic microorganisms in veterinary medicine and/or for the attainment of a growth-promoting action in the case of animals of commercial value, the compounds of the present invention can be combined with the following substances:

1. Antibiotics
   Penicillin and its derivatives,
   Cephalosporin and its derivatives,
   Chloramphenicol,
   Tetracyclines (e.g. chlorotetracycline, oxytetracycline),
   Rifamycin and its derivatives (e.g. Refampin)
   Lincomycin
   Bacitracin and its salts,
   Pyrrolnitrin
   Myxin,
   Streptomycin
   Nigericin
   Parvulin
   Spiramycin
   Neomycin
   Thiopeptin
   Tylosin.
2. Sulphonamides
   N'-(3,4-dimethyl-5-isoxazolyl)-sulphanilamide,
   N'-2-pyrazinylsulphanilamide,
   2,4-dimethoxy-6-sulphamylamido-1,3-diazine,
   N'-(4-methyl-2-pyrimidyl)-sulphanilamide.
3. Nitrofurans
   3-(5-nitrofurfurylideneamino)-2-oxazolidinone,
   5-morpholinomethyl-3-(5-nitrofurfurylideneamino)-2-oxazolidinone,
   3-amino-6[2-(nitro-2-furyl)vinyl]-pyridazine,
   1,5-di-(5'-nitro-2'-furyl)-penta-1,4-dien-one-(3)-2''-amidinohydrazone-hydrochloride.
4. Diaminopyrimidines
   2,4-diamino-5-(3,4,5-trimethoxybenzyl)-pyrimidine,
   2,4-diamino-5-(3,4-dimethoxybenzyl)-pyrimidine,
   2,4-diamino-5-(p-chlorophenyl)-6-ethylpyrimidine,
   2,4-diamino-5-(2-methyl-3,4-dimethoxybenzyl)-pyrimidine.
5. Hydroxyquinolines
   5,7-dichloro-8-hydroxyquinaldine,
   5-chloro-7-iodo-8-hydroxyquinoline.
6. Hydroxyquinolinecarboxylic acids and hydrozynaphthyridine acids
   1-ethyl-1,4-dihydro-7-methyl-4-oxo-1,8-naphthyridine-3-carboxylic acid,
   oxolinic acid.
7. Quinoxaline-di-N-oxides
   quinoxaline-1,4-di-N-oxide,
   3-(1,4-dioxo-2-quinoxalinemethylene)-carbazinic acid methyl ester.
8. Halogenated hydroxydiphenyl ethers
   2-hydroxy-2'4,4'-trichloro-diphenyl ether.
9. Nitrohydroxydiphenyl ethers
10. Optionally halogenated salicylic acid anilides
11. Triarylmethylimidazoles
    di-(phenyl)-2-chlorophenyl-imidazolyl(1)-methane.
12. Vitamins
13. 3-Hydroxy-2-methyl-4-pyrone
14. 2-Mercaptoimidazole
15. Ethoxylated alcohols
    such as $R-O(CH_2CH_2O)_nH$.
16. 2-Bromo-5-nitrothiazole
17. Guanidines
18. N-Substituted aminoacetic acids
19. β-Nitropropionic acid
20. Phenylcyclopropylamine
21. 2-(4-Thiazolyl)-benzimidazole
22. Piperazine and its salts
23. Benzodiazepinone derivatives
24. Dihydroxydiphenylsulphides
25. 4,5-Dihydroxy-2,4,6-octatrienedicarboxylic acids
26. 2-Formyl-4-chlorophenoxyacetic acids
27. Straight-chain aliphatic alcohols
28. 2-Chloro-10-(3-dimethylaminopropyl)-phenothiazine
29. Acetoxybenzoic acid
30. Auxins
    3,5-di-sec.butyl-α,β,δ-trihydroxy-1-cyclopentene-valeric acid,
    3,5-di-sec.butyl-δ-hydroxy-β-oxo-1-cyclopentene-valeric acid.

Determination of the minimum inhibiting concentrations (MIC) against bacteria and fungi Stock solutions (1.5) of the compounds of formula I in methylcellosolve are prepared, and these subsequently diluted so that the incorporation of 0.3 ml of the stock solution in each case and of each dilution in 15 ml each time of warm nutrient-agar produces a concentration series of 300, 100, 30, 10, 3, 1, and so forth, ppm of active substance in the agar. The mixtures whilst still warm are poured into dishes and, after solidification, inoculated with the following test organisms:

Gram-positive bacteria

*Staphylococcus aureus,*
*Sarcina ureae,*
*Streptoococcus faecalis,*
*Streptococcus agalactiae,*
*Corynebacterium diphteroides,*
*Bacillus subtilis,*
*Mycobacterium phlei.*

Gram-negative bacteria

*Escherichia coli,*
*Salmonella pullorum,*
*Salmonella cholerae-suis,*
*Bordetella bronchiseptica,*
*Pasteurella multocida,*
*Proteus vulgaris.*
*Proicus rettgeri,*
*Pseudomonas fluorescens,*
*Pseudomonas aerogenosa.*

Fungi

*Trichophyton gypseum,*
*Trichophyton gallinae,*
*Trichophyton verrucosum,*
*Candida albicans,*
*Candida krusci,*
*Aspergillus niger,*
*Aspergillus flavus,*
*Penicillium funiculosum,*
*Penicillium expansum,*
*Trichoderma viride,*
*Fusarium oxysporum,*
*Chaetonium globosum,*

*Alternaria tenuis,*
*Paecilomyces varioti,*
*Stachybotrys atra.*

After an incubation of 48 hours at 37° C. (bacteria) and 5 days at 28° C. (fungi), the minimum concentration (ppm) of the active substances with which the growth of the test organisms is inhibited is determined.

The recorded values for the minimum inhibiting concentration (MIC) in the case of compounds of formula I are clearly below the starting concentration of 300 ppm.

EXAMPLE 1

3-isobutoxycarbonylamino-7-methyl-1,2,4-benzotriazine-1,4-di-N-oxide

An amount of 27 g (0.14 mole) of 3-amino-7-methyl-1,2,4-benzotriazine-1,4-di-N-oxide is placed into 200 ml of dioxane, and an addition then made at 10° C. of 16.7 g (0.21 mole) of pyridine. To this suspension there is added, in the course of 30 minutes, 28.6 g (0.21 mole) of dichloroformic acid isobutyl ester, with a slight exothermic reaction of the mixture resulting. Stirring is performed overnight at room temperature, and the reaction mixture is then filtered under suction. The filtrate is concentrated in vacuo to dryness. The product obtained is suspended in water, filtered off with suction, dried, and recrystallised from 100 ml of acetonitrile.

Yield: 15 g (43%); M.P. 150°–153° C.

EXAMPLE 2

3-Thenoylamino-7-methoxy-1,2,4-bezotriazine-1,4-di-N-oxide 14,6 g (0,1 mole) 2-thienylcarbonic acid chloride is added dropwise to a suspension of 20,7 g (0,1 mole) 3-amino-7-methoxy-1,2,4-benzotriazine-1,4-di-N-oxide in 300 ml dioxane and 7,9 g pyridine. This mixture is stirred overnight at room temperature and subsequently filtered.

The residue is suspended in water and then filtered, washed with water and subsequently methanol and dried under vacuum.

Yield: 25 g; M.P. 179°–181° C.

EXAMPLE 3

3-(2,4'-Dichlorobenzylureido)-7-metyl-1,2,4-benzotriazine-1,4-di-N-oxide 8,05 g (0,0456 mole) 2,4-dichlorobenzylamine is added to a suspension of 10,0 g (0,0456 mole) 5-oxo-1,2,4-oxodiazolo-(2,3-3,4)-7-methyl-1,2,4-benzotriazine-mono-N-oxide in 200 ml dioxane at room temperature. The reaction proceeds exothermically and a brown solid commences precipitating from the originally obtained violet solution. The mixture is stirred overnight at room temperature, the formed solid filtered off, washed with dioxane and suspended in 100 ml ethanol. This suspension is heated to 70° C. for 5 minutes, the solid is subsequently filtered off and dried.

Yield: 12.9 g; M.P. 210°–215° C.

EXAMPLE 4

N,N-dimethyl-N'-[7-methyl-1,2,4-benzotriazinyl(3)-1,4-di-N-oxide]-formamidine

An amount of 14.4 g (0.075 mole) of 3-amino-7-methyl-1,2,4-benzotriazine-1,4-di-N-oxide is placed into 150 ml of methylcellosolve at 50° C. In the course of 40 minutes, 9 g (0.075 mole) of dimethylformamidinedimethylacetal is added dropwise. The whole is subsequently stirred for 2 hours at 50° C. and overnight at room temperature. The red precipitate is filtered off with suction, then washed with methanol and dried.

Yield: 15 g (80%); M.P. 196°–198° C.

EXAMPLE 5

The following compounds were produced by methods analogous to those described in the preceding examples:

| | | |
|---|---|---|
| 1 | 3-benzyloxycarbonylamino-1,2,4-benzotriazine-1,4-di-N-oxide | M.P. 146° C. |
| 2 | 3-(pyridyl-3-)-ureido-1,2,4-benzotriazine-1,4-di-N-oxide | M.P. 181°–183° C. |
| 3 | 3-(phenylethylureido)-1,2,4-benzotriazine-1,4-di-N-oxide | M.P. 188°–189° C. |
| 4 | 3-(3',4'-dichlorphenylpropylureido)-7-methyl-1,2,4-benzotriazine-1,4-di-N-oxide | M.P. 193°–195° C. |
| 5 | 3-benzylureido-1,2,4-benzotriazine-1,4-di-N-oxide | M.P. 184°–186° C. |
| 6 | 3-(p-chlorophenylethylureido)-1,2,4-benzotriazine-di-N-oxide | M.P. 202°–204° C. |
| 7 | 3-benzylureido-7-methyl-1,2,4-benzotriazine-1,4-di-N-oxide | M.P. 192°–194° C. |
| 8 | 3-(2',4'-dichlorophenylpropylureido)-7-methyl-1,2,4-benzotriazine-1,4-di-N-oxide | M.P. 200°–202° C. |
| 9 | 3-(phenylpropylureido)-1,2,4-benzotriazine-1,4-di-N-oxide | M.P. 168°–171° C. |
| 10 | 3-(p-chlorophenylethylureido)-7-methyl-1,2,4-benzotriazine-1,4-di-N-oxide | M.P. 212°–214° C. |
| 11 | 3-(phenylbutylureido)-7-methyl-1,2,4-benzotriazine-1,4-di-N-oxide | M.P. 199°–202° C. |
| 12 | 3-(2',6'-dichlorophenylethylureido)-7-methyl-1,2,4-benzotriazine-1,4-di-N-oxide | M.P. 210°–213° C. |
| 13 | 3-(2',4'-dichlorobenzylureido)-1,2,4-benzotriazine-1,4-di-N-oxide | M.P. 204°–208° C. |
| 14 | 3-(phenylbutylureido)-1,2,4-benzotriazine-1,4-di-N-oxide | M.P. 174°–178° C. |
| 15 | N,N-dimethyl-N'[1,2,4-benzotriazinyl(3)-1,4-di-N-oxide]formamidine | M.P. 182° C. |
| 16 | N,N-dimethyl-N'[7-methyl-1,2,4-benzotriazinyl(3)-1,4-di-N-oxide]acetamidine | M.P. 168°–170° C. |
| 17 | 3-furoylamino-7-methoxy-1,2,4-benzotriazine-1,4-di-N-oxide | M.P. 194°–198° C. |

| | -continued | |
|---|---|---|
| 18 | 3-thenoyl-7-chloro-1,2,4-benzotriazine-1,4-di-N-oxide | M.P. 201°–202° C. |
| 19 | 3-[oxazolidon(2')yl-(3')ureido]-1,2,4-benzotriazine-1,4-di-N-oxide | M.P. 182°–184° C. |
| 20 | N,N-dimethyl-N'-[7-phenoxy-1,2,4-benzotriazinyl(3)-1,4-di-N-oxide]-formamidine | M.P. 185°–197° C. |
| 21 | N,N-dimethyl-N'-[7-chloro-1,2,4-benzotriazinyl(3)-1,4-di-N-oxide]-formamidine | M.P. 193°–195° C. |
| 22 | N,N-dimethyl-N'-[7-methoxy-1,2,4-benzotriazinyl(3)-1,4-di-N-oxide]-formamidine | M.P. 192°–194° C. |
| 23 | N,N-dimethyl-N'[7-chloro-1,2,4-benzotriazinyl(3)-1,4-di-N-oxide]-acetamidine | M.P. 186°–188° C. |

EXAMPLE 6

Comparative Experiment for Demonstrating Growth Promotion in poultry 100 ppm of each of the following compounds was added to standard poultry feed and fed to 80 pullets divided into 8 groups each of 10 animals (four groups male and four female). At the start of the test the pullets were one day old. During the test which lasted 28 days, the pullets were kept in cages. For control purposes, a similar group of pullets was fed with the same standard feed but without the active substance. All animals were weighed at the start and end of the test. To measure the effectiveness of the tested compounds, the weight difference of the test animals was compared with that of the control animals.

Compounds A-G represent compounds of the instant invention while compounds H-K represent compounds of U.S. Pat. No. 3,957,779.

Compounds tested

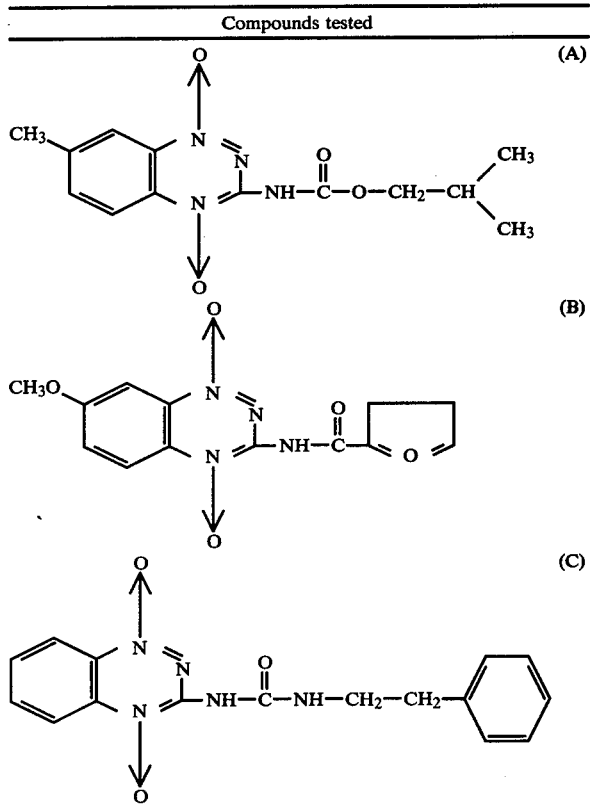

(A)

(B)

(C)

Compounds tested

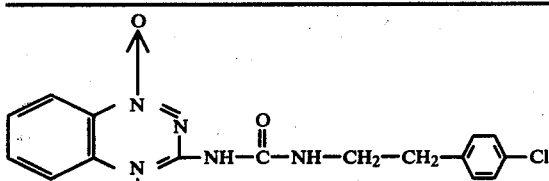

(D)

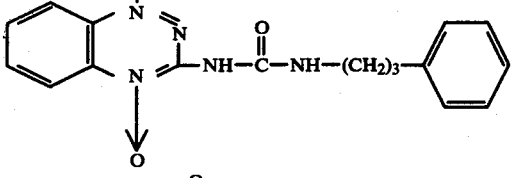

(E)

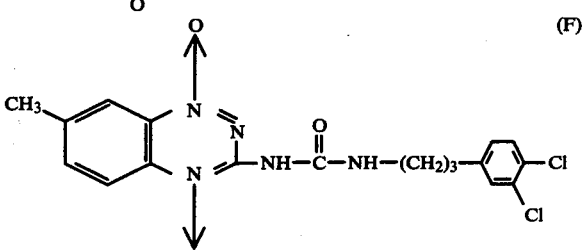

(F)

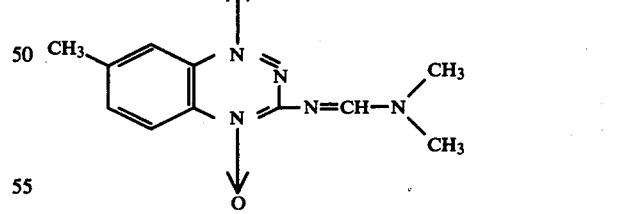

(G)

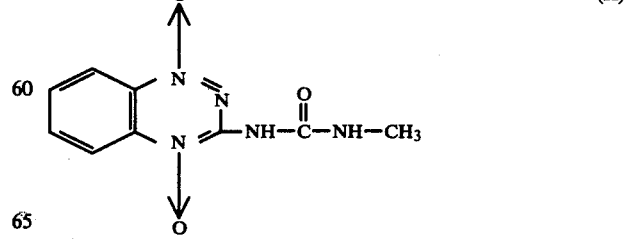

(H)

-continued

Compounds tested

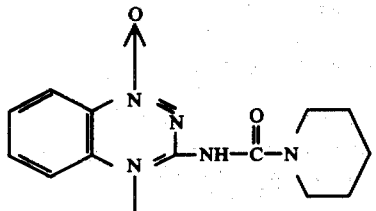

| Results Compounds | Growth promotion rate in % |
|---|---|
| A | + 6,2 |
| B | + 6,1 |
| C | + 6,8 |
| D | + 6,7 |
| E | + 7,8 |
| F | + 7,1 |
| G | + 7,0 |
| H | + 3,7 |
| I | + 4,2 |
| J | + 3,4 |
| K | − 2,3 |

CONCLUSION

The above data show clearly that compounds A–G of the instant application are markedly superior to prior art compounds H–K with respect to their growth promoting activity.

EXAMPLE 7

Feed additive: The following food mixtures were prepared to obtain 6 kg samples of final feed containing respectively (a) 25 ppm, (b) 50 ppm, (c) 200 ppm and (d) 400 ppm of active substance:

(a)

0.15 parts by weight of one of the compounds according to formula I,
49.85 parts by weight of bolus alba,
150.0 parts by weight of standard feed for poultry, pigs or ruminants;

(b)

0.30 parts by weight of one of the compounds according to formula I,
44.70 parts by weight of bolus alba,
5.0 parts by weight of silicic acid,
150.0 parts by weight of standard feed for poultry, pigs or ruminants;

(c)

1.2 parts by weight of one of the compounds according to Formula I,
43.8 parts by weight of bolus alba,
5.0 parts by weight of silicic acid,
150.0 parts by weight of standard feed for poultry, pigs or ruminants;

(d)

2.4 parts by weight of one of the compounds according to formula I,
47.6 parts by weight of bolus alba,
150.0 parts by weight of standard feed for poultry, pigs or ruminants.

The supplementary feed according to the invention is administered either by being mixed direct with the carriers, or by being drawn on to the carriers after it has been dissolved, for example, in chloroform. The material is subsequently ground to obtain the desired particle size of, e.g. 5–10 microns. These feed premixes are mixed with 5800 parts by weight of standard feed, or are processed into 6000 parts by weight of finished drinking liquid. Furthermore, these feed premixes can be treated to give 6000 parts by weight of standard feed in the form of pellets.

Pigs and ruminants fed with the above-mentioned feed mixtures clearly show the growth-promoting action of the said feed mixtures, compared with the control animals fed with corresponding feed mixtures and preparations not containing the active substances according to the invention.

In the rearing of animals of commercial value, such as pigs, poultry and ruminants, e.g. cattle, calves and sheep, it is desirable for economic reasons to obtain, in the shortest possible time, maximum meat, milk and egg yields with the smallest possible amount of feed. It is suggested according to the invention that, in order to obtain this result, the compounds of formula I be used as feed additives for the said productive animals.

The active substances of formula I to be used according to the invention are added, either direct or in the form of a premix, to the feed or to the drinking troughs of the aforementioned animals, the applied amounts being 1 to 500 ppm relative to the total amount of feed or drinking liquid.

Suitable premixes consist, e.g. of a mixture of the active substance with kaolin, lime, aluminium oxide, ground shells, bolus alba, aerosil, starch or lactose. A feed mixture is prepared by the thorough mixing of the necessary amount of premix with the appropriate amount of a commercial standard feed.

There can be added to the feed mixture further substances which favourable influence the growth and development of the animals. Such additives are, in particular, vitamins, mineral salts, antibiotics, nitrofurans, diaminopyrimidines, hydroxyquinolines, hydroxyquinolinecarboxylic acids, quinoxaline-di-N-oxides, etc.

What is claimed is:

1. A 1,2,4-benzotriazine-1,4-di-N-oxide derivative of the formula I

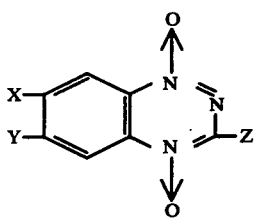

(I)

wherein

X and Y each independently represents hydrogen, alkyl or alkoxy having 1 to 4 carbon atoms, phenoxy, or halogen, and Z stands for the group of the formula

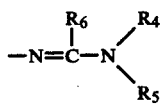

wherein $R_4$ and $R_5$ each independently represents hydrogen or alkyl having 1 to 4 carbon atoms and $R_6$ represents hydrogen or methyl.

2. N,N-dimethyl-N'-[7-methyl-1,2,4-benzotriazinyl(3)-1, 4-di-N-oxide]-formamidine according to claim 1.

3. A composition for the control of pathogenic microorganisms, which composition contains as active substance an effective amount of a compound according to claim 1.

4. A composition for combatting respiratory diseases caused by E. coli airsacculitis in poultry, which composition contains as active substance an effective amount of a compound according to claim 1.

5. A composition for promoting the growth of domestic animals and productive livestock, which composition contains as active substance an effective growth promoting amount of a compound according to claim 1.

6. A method of combatting pathogenic microorganisms, which comprises administering to the host afflicted with said microorganisms an effective amount of a compound according to claim 1.

7. A method of combatting diseases of the respiratory tract in poultry caused by E. Coli which comprises administering to said poultry an effective amount of a compound according to claim 1.

8. A method of promoting the growth of domestic animals and productive livestock, which comprises administering to said animals and livestock an effective growth promoting amount of a compound according to claim 1.

* * * * *